United States Patent [19]

Ward et al.

[11] Patent Number: 5,132,221

[45] Date of Patent: Jul. 21, 1992

[54] LYSOGENIC BACTERIOPHAGE ISOLATED FROM ACIDOPHILIUM

[75] Inventors: Thomas W. Ward; Debby F. Bruhn; Deborah K. Bulmer, all of Idaho Falls, Id.

[73] Assignee: The United States of America as represented by the United States Department of Energy, Washington, D.C.

[21] Appl. No.: 350,662

[22] Filed: May 10, 1989

[51] Int. Cl.$^5$ .................. C12N 7/00; C12N 1/20
[52] U.S. Cl. ................. 435/235.1; 435/252.1; 435/320.1; 935/31
[58] Field of Search ............ 435/235.1, 172.3, 320.1, 435/252.1; 935/31

[56] References Cited

U.S. PATENT DOCUMENTS

| 4,711,849 | 12/1987 | Rawling et al. | 435/172.3 |
| 4,716,114 | 12/1987 | Nicolau et al. | 435/172.3 |
| 4,748,118 | 5/1988 | Rawling et al. | 435/172.3 |

OTHER PUBLICATIONS

Katayama et al. (1982), J. Gen. Micro., vol. 128, pp. 1599-1611.
Tomizuka et al. (1976), Agr. Biol. Chem., vol. 40, p. 1019-1025.
Ackerman et al. (1982), Asm News, vol. 48, pp. 346-348.
Bergey's Manual of Systematic Bacteriology (1989), vol. 3, pp. 1842-1845, 1850, 1863-1865.
Johnson et al. (1973), J of Virology, vol. 12, pp. 1160-1163.
Davidson et al. (1983), Appl. Environ. Microbiol., vol. 46, pp. 565-572.

Primary Examiner—Richard A. Schwartz
Assistant Examiner—Richard M. Lebovitz
Attorney, Agent, or Firm—James W. Weinberger; Thomas G. Anderson; William R. Moser

[57] ABSTRACT

A bacteriophage identified as $\phi Ac1$ capable of infecting acidophilic heterotropic bacteria (such as *Acidiphilium sp.*) and processes for genetically engineering acidophilic bacteria for biomining or sulfur removal from coal are disclosed. The bacteriophage is capable of growth in cells existing at pH at or below 3.0. Lytic forms of the phage introduced into areas experiencing acid drainage kill the bacteria causing such drainage. Lysogenic forms of the phase having genes for selective removal of metallic or nonmetallic elements can be introduced into acidophilic bacteria to effect removal of the desired element form ore or coal.

1 Claim, 1 Drawing Sheet

LYSOGENIC BACTERIOPHAGE ISOLATED FROM ACIDOPHILIUM

CONTRACTURAL ORIGIN OF THE INVENTION

The United States Government has rights in this invention pursuant to Contract No. DE-AC07-76ID01570 between the United States Department of Energy and EG&G Idaho, Inc.

BACKGROUND OF THE INVENTION

Genetic engineering of bacteria is well-known, however one such method, transduction, is less practiced. Transduction involves the use of a bacterial virus (or bacteriophage) to deliver DNA (contained in the virus) into the cell it infects. Inserting a desired sequence of base pairs in a phage is considerably easier than doing so in a bacteria since the DNA molecule of a bacteriophage is relatively small when compared with that of a bacteria. Therefore, if the DNA molecule of a bacteriophage is "engineered" by manipulation of its sequence, and the bacteriophage then intentionally introduced to a population of bacteria under conditions promoting infection and consequent transduction, the bacteria can be "genetically engineered" in a relatively simple process.

Conventional genetic engineering utilizes the transfer of plasmids, a less stable method of changing the DNA composition of an organism than transduction, which results in the desired DNA sequence being inserted directly into the host chromosome. Therefore, in the latter case one is assured that the inserted genetic material will be carried to subsequent generations after replication.

One of the environments in which bacteria flourish and potentially are of great economic benefit or detriment, is in acidic ambient temperature environments, such as mined ore or coal, tailings dumps, or the like. Such accumulations of ore, coal or tailings conventionally occur in large quantities, sometimes involving many thousands of tons spread over many acres.

Three related microorganism-based processes are all relevant to these environments and the present invention: first, the removal of sulfur from coal prior to its burning (thereby reducing subsequent release of sulfur oxides), secondly, the "biomining" of valuable metals from mined ore deposits, and thirdly, the prevention of acid leaching from tailings deposits of processed ore and from abandoned coal or metal mines. Each of these phenomena may be accomplished by introducing bacteriophage DNA into appropriate bacteria to effect the desired process. By placing genetically engineered organisms into the appropriate location in the first two processes noted above, or by placing selected bacteriophage into the acidic environment under conditions that promote infection and lysis of the resident bacteria in the third process, the response of the bacteria to their environment can be altered.

For instance, naturally occurring bacteria such as Thiobacillus ferrooxidans are found in sulfur-containing coal deposits. Thiobacillus readily attacks inorganic (pyritic) sulfur but not organic sulfur. Thus far, no microorganism has been found which is capable of removing both organic and inorganic forms of sulfur from coal—complete microbiological removal of sulfur from coal may be currently accomplished only by sequential treatment using completely different conditions. The time, expense and technical difficulties associated with such a two step procedure renders it impractical and uneconomic, and it is not currently practiced.

Likewise, acidic leaching from tailings piles and abandoned coal and metal mines at pHs of from 1.5 to bout 5.0 occurs because of sulfide oxidation by Thiobacillus sp ultimately resulting in sulfuric acid. Procedures are currently available to either kill such bacteria or render them inactive, but such procedures involve the application of chemicals (such as sodium dodecyl sulfate alone or combined with organic acids) in large quantities to the tailings piles, which are expensive and are in and of themselves environmentally objectionable. The introduction of a naturallyoccurring biological control agent, such as a bacteriophage, would be a preferable method of controlling acid leaching.

Finally, acidophilic heterotrophic bacteria which normally inhabit valuable metal-containing ores are tolerant of the normally toxic metals and low pHs associated with such environments, but do not have the genetic capability to enable these bacteria to "leach" the valuable metal. Such leaching may occur in a number of ways, but primarily through the microbial production of sulfuric acid in situ which leaches many metals from the surrounding ore. A bacteria capable of surviving such conditions which is genetically engineered to render such valuable metals more readily available for extraction would reduce the significant costs incurred in processing huge quantities of ore for recovery of relatively small amounts of the particular valuable metals.

For example, biooxidation of refractory arsenical sulfide concentrates for gold recovery indicates that recovery of available gold can be increased from about 66 percent using cyanide alone, to about 95 percent when used in conjunction with biological processes. The rate of biooxidation of ores is governed by substrate concentration, accessibility and the amount and specific activity of the biologically-produced enzymes involved. The amount of enzyme is usually proportional to the biomass, which is a result of the rate of growth of the microorganism. The processes as contemplated herein do not generate significant amounts of heat and thus would use naturally-occurring heterotrophic bacteria, rather than the thermophilic bacteria used in some industrial processes.

Heretofore, researchers in this area have failed to identify bacterial viruses capable of infecting and, thereby, potentially genetically engineering, bacteria found in such highly acidic environments. It is believed by some that such procedures are not possible at this time. Therefore, it is an object of this invention to provide, specifically, a bacteriophage capable of infecting acidophilic heterotrophic bacteria so as to deliver a desired DNA sequence into the host bacteria. It is a further object of the invention to provide processes whereby such genetically engineered bacteria are enabled to perform a function heretofore impossible.

SUMMARY OF THE INVENTION

The present invention discloses a novel bacteriophage, and a process for using bacteriophages in acidophilic bacteria in general. The specific phage of this invention is designated $\phi$Acl and is deposited in ATCC under accession Nos. 55305 and 55306. Such deposit is available under conditions set forth in 37 CFR. Access to such organism should not be considered a license to use the organism except as provided by law.

Bacteriophage φAcl is capable of infection of and lysogenic growth in the genus Acidiohilium at pHs of from about 2.0 to about 5.0. The phage itself exhibits optimal stability outside the cell at about pH 5.0 in certain media. The significance of phage φAcl is that, for the first time, a vector for genetic engineering of acidophilic bacteria via transduction is available. Three broad categories of use of such a bacteriophage system are: (1) prevention of acid leaching from abandoned tailings piles and coal mines, (2) enhancing or improving the biomining of valuable metals from mined ore and (3) removal of sulfur from mined coal prior to burning. The first of these processes involves the introduction of lytic forms of the phage to acidophilic bacteria that are causing acid drainage at mine tailings and abandoned coal mine sites. The bacteria would therefore be killed in situ. The second and third processes would involve removal of naturally occurring bacteria from the ore deposits or coal piles genetically engineering them in the laboratory by introducing specific genes into the bacterial DNA using phage transduction, and reintroduction of the bacteria to the site to be "processed". The genes inserted into the bacteria by the phage enable the bacteria to selectively remove metals or sulfur from the ore or coal.

DETAILED DESCRIPTION OF THE INVENTION

Figure 1:
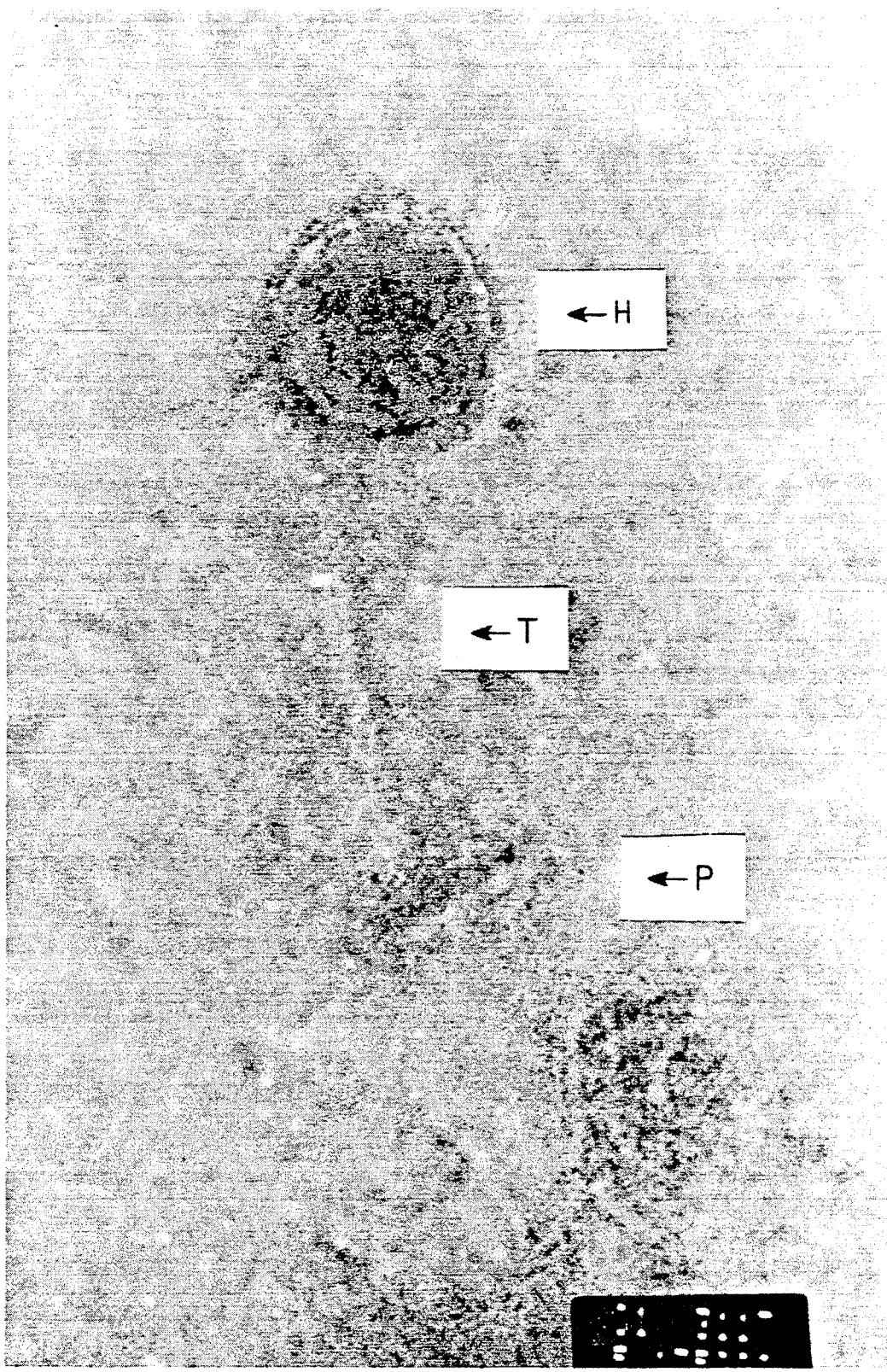
FIG. 1 is an electron micrograph of the bacteriophage φAcl of the present invention.

The genus Acidiphilium contains acidophilic, heterotrophic, aerobic, gram-negative eubacteria, which are commonly isolated from acidic mine environments. The literature contains very little by way of disclosure of bacterial viruses (bacteriophages) capable of infecting such organisms. A bacteriophage, named φAcl and deposited in the ATCC under accession Nos. 55305 and 55306 has been discovered, and several properties of the bacteriophage relating to commercially significant processes have been investigated.

The bacteriophage of the present invention has been shown to infect certain strains of Acidiphilium and to be a lysogenic phage of these cells. A number of Acidiphilium strains set forth in Table 1 below and identified with the "CM" prefix were isolated from water collected at the Blackbird cobalt mine near Salmon, Id. The remaining strains were acquired from readily available sources. Applicants have determined that after infection with φAcl, a significant fraction of Acidiphilium cells incorporate the bacteriophage genetic material and are not killed. It has been observed that these Acidiphilium cells are resistant to further infection, as is the rule with lysogenic phage.

Conjugation between acidophilic bacteria has not been demonstrated. While plasmids have been observed in Acidiphilium and acidophilic Thiobacillus, with one exception (relating to uranium resistance) such plasmids are cryptic. Likewise, successful DNA-mediated transformation has not been reported in the literature for such species.

Experiments have been conducted to determine the specific properties of φAcl, and how it may be useful to effect genetic engineering of certain naturally occurring bacteria for use in industrial processes.

The bacteriophage φAcl is described as follows:

| | | |
|---|---|---|
| a. | Morphology: | similar to lambda with a polyhedral head (H), a long thin tail (T) and, possibly a base plate (P) at the end of the tail. The head diameter is about 78 mm. |
| b. | Life Cycle: | from initial infection until the host cell lyses and liberates phage particles is about 3 hours, +/− 15 minutes. Approximately 60 phage particles are released from each infected cell (range about 40–80). |
| c. | Nucleic Acid: | double stranded DNA. Approximate number of base pairs is 97,000. |
| d. | Host Interaction: | southern blot analysis and isolation of lysogens from plaques indicate the phage is lysogenic. Cells resistant to the phage can be isolated from plaques produced on sensitive cells. These resistant cells harbor the phage and behave similarly to original donor cells. |
| e. | Stability: | pH outside the cell is 5.0, ideal pH for growth of the phage in cells is 3.0 (which is the ideal pH for growth of the cell). |
| f. | Restriction Enzyme Analysis: | restriction enzyme map is not known, but the phage DNA is protected from digestion by several restriction enzymes as shown by agarose gel electrophoresis and southern blot analysis. |
| g. | Sedimentation Coefficient: | about 655S, or about 1.57 times that of lambda. |

EXAMPLE 1

Acidiphilium strains were grown in liquid glycerol salts media adjusted to a pH of 3.0 plus 0.01 percent yeast extract. The phase was plated in top agarose consisting of glycerol salts media with 0.01 percent yeast extract and 0.3 percent agarose. Acidiphilium donor strains were grown to densities of $1-5 \times 10^7$ cells/ml at room temperature in glycerol salts media. Donor cells were centrifuged, resuspended and irradiated in 5 ml aliquots for 25 seconds with a 15-watt germicidal ultraviolet lamp at a distance of 60 cm. Irradiated donor cells were mixed with sensitive cells and the mixture incubated for 15 minutes at room temperature. The mixture was then added to 3–4 mls of top agarose at 45° C., plated and incubated for 24–30 hours at 32° C. Phage buffer was added and the top agarose from all plates was scraped into a 50 ml tube. After adjusting the pH to 5.0 and incubating for 5 hours at 4° C., the tube was centrifuged to remove agarose and debris. The supernant was filtered through a 0.45 micron filter and stored at 4° C.

For determining plaque forming units (PFU) mixtures of phage or donor cells with sensitive cells were made, and added to top agarose and plated as above. After incubation at 32° C. for 24–48 hours, plaques were counted.

Filtered preparations of the phage were fixed with 0.6 percent glutaraldehyde, mounted on carbon-coated copper grids and negatively stained with 1 percent uranyl acetate.

The search for an appropriate bacteriophage involved testing the various strains of bacteria in the laboratory for the presence of an endogenous bacteriophage. A series of pai treatments was thus performed in which cells of one strain were irradiated with UV light and a small number of these cells were mixed with a large number of cells of a second strain, followed by plating in soft agarose. Initially, plaques containing phage particles were produced when donor cells were mixed with recipient cells, but filtered phage preparations produced no plaques or very few plaques when mixed with sensitive cells. Finally, it was determined that the bacteriophage is very unstable when kept in the growth medium outside the cell at a pH of about 3.0. It was determined that optimal phage stability in that medium occurred at a pH of about 5.0 rather than at the optimal cell growth pH of 3.0 or the presumed internal pH of the recipient cells of about 7.0.

As set forth in Table 1 below,

TABLE 1

Susceptibility of Various Acidiphilium Strains to Phage Infection

| Strain | Spot Test | Titer |
|---|---|---|
| CM3(s) | + | $3 \times 10^5$ |
| CM9(s) | + | $6 \times 10^4$ |
| CM1(d) | ± | 0 |
| CM3A(d) | ± | 0 |
| CM9A(d) | ± | 0 |
| CM4 | − | 0 |
| CM4A | − | 0 |
| CM5 | + | $7 \times 10^4$ |
| CM7 | − | 0 |
| AWB | ± | 0 |
| BBW | + | 0 |
| GGW | + | 0 |
| KLB | − | ND |
| LHet | − | ND |
| OP | − | ND |
| PW1 | − | 0 |
| PW2 | + | $8 \times 10^4$ |
| QBP | − | ND |

+ Large clear plaque.
± Few Small plaques in treated area.
− No lysis.
ND Not determined.
Spot test: 100–300 microliters of sensitive cells were mixed with top agarose and poured on 60 mm dishes. After the top agarose hardened, 10–20 microliters (1–5 × $10^4$ PFU) of phage were placed on the nascent lawns along with equivalent drops of buffer. Assays were scored after 24–48 hours.
Titer: Serial dilutions of a phage preparation were titered on each strain.
(s) Sensitive, indicator cells used.
(d) Phage-carrying donor cells ("lysogen").

four Acidiphilium strains were shown to support replication of bacteriophage φAcl. Strains BBW and GGW exhibit anomalous behavior, interpreted as death of the cells resulting from phage infection. However, the phage cannot replicate in these two strains, explaining the lack of plaques in the titer test.

Electron microscopy (FIG. 1) indicates the phage φAcl to have a morphology similar to lambda with a polyhedral head (H), a long thin tail (T) and, possibly a base plate (P) at the end of the tail. The head has a diameter of approximately 78 mm. The phage is lysogenic, as cells resistant to the phage can be isolated from plaques produced on sensitive cells by filtered phage preparations.

Further details of the above experiment are available in *Biotechnology in Minerals and Metal Processing*, Scheiner, et al, Society of Mining Engineers, Inc., Littleton Col., 1989.

EXAMPLE 2

Acidiphilium strains CM9 and CM9A were grown in glycerol salts medium as set forth above. Bacteriophage φAcl was stored and diluted in phage buffer. Plate lysates were prepared by mixing $6.5-7.0 \times 10^3$ PFU of phage with 0.4–0.5 ml of mid-log ($5 \times 10^7$/ml) sensitive cells and 3.2 mls soft agarose at 45° C. Plates were incubated at 32° C for 15–24 hours and thereafter treated as set forth in Example 1.

Phage stocks were assayed for nucleic acid. Isolated nucleic acid was dialyzed extensively against TE (10 mM Tris, 1 mM EDTA pH 7.5). Restriction enzyme and S1 nuclease digestions were carried out according to manufacturer's instructions. DNA samples were electrophoresed on 0.8 percent agarose gels in 0.5X TBE. An M.J. Research programmable power inverter was used to control electrophoresis of samples.

The results indicate that φAcl nucleic acid is linear double-stranded DNA. The virion nucleic acid is completely digested by DNAse I, but not by RNAse A. Unheated DNA is not digested by S1 nuclease but heat denatured φAcl DNA is completed digested. The molecular weight of φAcl DNA has been estimated using field inversion gel electrophoresis to be approximately 97,000 base pairs. A similar size was obtained when the molecular weight was estimated using electron microscopy.

The discovery of the bacteriophage φAcl which is capable of lysogenic growth on strains of the genus Acidiphilium opens significant new opportunities for the genetic engineering of acidophilic heterotrophic bacteria. In a first embodiment, genetically engineered acidophilic heterotrophs may directly or indirectly increase the rate of leaching of valuable metals from mined ore deposits, and may be usable in a unified process for removing both organic and inorganic sulfur from coal. Typically, an aqueous solution is caused to flow through the area subjected to the microbial action. In order to increase the effectiveness of the acidophilic bacteria, the aqueous solution should preferably contain a nutrient such as ammonium phosphate. Metals such as gold, silver, cobalt, copper, cadmium, nickel, zinc and molybdenum and nonmetallic elements such as sulfur, can be removed by this process. Such list is not exhaustive—several other metal and nonmetallic elements can be removed by this process. Whether or not φAcl is the operative agent in these procedures, demonstration of a bacteriophage of such organisms proves the viability of such procedures.

The experiments reported above indicate that not all of the infected cells survive the infection—a significant number are killed as a result of infection by φAcl. In a second embodiment of the invention, creation of a virulent mutant of φAcl which would kill all or almost all of the infected cells would permit biological control of the infected cell type. Such procedures would be selective for the particular bacteria to be controlled—bacteriophage-host interactions are highly specific and the bacteriophage would have no effect on non-target bacteria or other organisms. Thiobacillus is similar in many respects to Acidiphilium, and is responsible for most of the acidic leaching which occurs in mine tailings and abandoned coal mines. Naturally occurring phage in Thiobacillus strains may yet be found, one or more of which may be mutated to produce a virulent strain capable of biological control. Virulent mutants of φAcl capable of infecting Thiobacillus could substantially reduce, or almost totally eliminate, this acidic leaching or drainage from abandoned coal or metal mines.

Lastly, a third embodiment of this invention is for the microbial desulfurization of coal. Certain acidophilic bacteria are already known to attack pyritic (inorganic) sulfur in coal, such as *Thiobacillus ferrooxidans*. By using genetically engineered Thiobacillus incorporating transduced DNA coding for release of organic sulfur, most of the sulfur in a body of coal could be removed prior to burning by a single type of microorganism. Alternatively, another acidophilic heterotrophic bacteria such as Acidiphilium, genetically engineered to attack only organic sulfur, can be introduced cooperate with the naturally occurring Thiobacillus.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

We claim:

1. An isolated Acidophilium bacteriophage designated $\phi$ACl.

* * * * *